US00PP13692P29

(12) United States Plant Patent
McAllister

(10) Patent No.: US PP13,692 P2
(45) Date of Patent: Apr. 1, 2003

(54) BRACHYCOME PLANT NAMED 'METALLIC BLUE'

(75) Inventor: Margaret E. McAllister, Croydon (AU)

(73) Assignee: Outback Plants Pty. Ltd., Cranbourne (AU)

( * ) Notice: Subject to any disclaimer, the term of this patent is extended or adjusted under 35 U.S.C. 154(b) by 0 days.

(21) Appl. No.: 10/080,607

(22) Filed: Feb. 22, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Brachycome named 'Metallic Blue', characterized by its upright and rounded plant growth habit; large inflorescences with light violet-colored ray florets; and erect peduncles that hold inflorescences above the foliage.

2 Drawing Sheets

BOTANICAL CLASSIFICATION/CULTIVAR DESIGNATION

*Brachycome multifida* cultivar Metallic Blue.

BACKGROUND OF THE INVENTION

The present invention relates to a new and distinct cultivar of Brachycome plant, botanically known as *Brachycome multifida* and hereinafter referred to by the name 'Metallic Blue'.

The new Brachycome was discovered by the Inventor in Croydon, Victoria, Australia as a seedling from a random cross of two unidentified selections of *Brachycome multifida*, not patented. The new Brachycome was discovered and selected by the Inventor as a plant within the progeny of the stated cross in a controlled environment in Croydon, Victoria, Australia in 1991. The selection of the new Brachycome was based on its upright growth habit and inflorescences with light violet-colored ray florets. Compared to plants of the parent selections, plants of the new Brachycome have a more upright plant growth habit, darker green-colored leaves and larger inflorescences.

Asexual reproduction of the new Brachycome by cuttings taken in a controlled environment in Montrose, Victoria, Australia, since 1991, has shown that the unique features of this new Brachycome are stable and reproduced true to type in successive generations.

The new Brachycome has not been observed under all possible environmental conditions. The phenotype may vary somewhat with variations in environment such as temperature, daylength and light intensity without, however, any variance in genotype.

The following characteristics have been repeatedly observed and are determined to be basic characteristics of 'Metallic Blue' and distinguish the new Brachycome as a new and distinct cultivar:

1. Upright and rounded plant growth habit.

2. Large inflorescences with light violet-colored ray florets.

3. Erect peduncles that hold inflorescences above the foliage.

Plants of the new Brachycome can be compared to plants of the cultivar City Lights, disclosed in U.S. Plant Pat. No. 11,646. In side-by-side comparisons conducted in St. Richmond, Victoria, Australia, plants of the new Brachycome differed from plants of the cultivar City Lights in the following characteristics:

1. Plants of the new Brachycome were more upright and taller than plants of the cultivar City Lights.

2. Inflorescences of plants of the new Brachycome had fewer ray florets than inflorescences of plants of the cultivar City Lights.

3. Plants of the new Brachycome and the cultivar City Lights differed in ray floret coloration.

4. Inflorescences of plants of the new Brachycome had smaller discs than inflorescences of plants of the cultivar City Lights.

Plants of the new Brachycome can also be compared to plants of the cultivar Billabong Mauve Delight, disclosed in U.S. Plant Pat. No. 10,889. In side-by-side comparisons conducted in St. Richmond, Victoria, Australia, plants of the new Brachycome differed from plants of the cultivar Billabong Mauve Delight in the following characteristics:

1. Plants of the new Brachycome were more upright and taller than plants of the cultivar Billabong Mauve Delight.

2. Inflorescences of plants of the new Brachycome were larger and had more ray florets than inflorescences of plants of the cultivar Billabong Mauve Delight.

3. Plants of the new Brachycome and the cultivar Billabong Mauve Delight differed in ray floret coloration.

4. Plants of the new Brachycome had longer peduncles than plants of the cultivar Billabong Mauve Delight.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Brachycome.

The photograph on the first sheet comprises a side perspective view of a typical plant of 'Metallic Blue' grown in the landscape.

The photograph on the second sheet is a close-up view of typical inflorescences of 'Metallic Blue'.

DETAILED BOTANICAL DESCRIPTION

The aforementioned photographs and the following observations and measurements describe plants grown in St. Richmond, Victoria, Australia, in a polyethylene-covered greenhouse with open sidewalls with day temperatures ranging from 11 to 42° C., night temperatures ranging from 4 to 23° C., and light levels ranging from 5,000 to 9,000 foot candles. Rooted young plants of the new Brachycome were planted in 15-cm containers, pinched once about 4 to 6 weeks after planting, and grown for about 12 months. Color references are made to The Royal Horticultural Society Colour Chart, 1995 Edition, except where general terms of ordinary dictionary significance are used.

Botanical classification: *Brachycome multifida* cultivar Metallic Blue.

Parentage:

*Female or seed parent.*—Unidentified selection of *Brachycome multifida*, not patented.

*Male or pollen parent.*—Unidentified selection of *Brachycome multifda*, not patented.

Propagation:

*Type.*—By cuttings.

*Time to initiate roots.*—Summer: About 10 to 25 days at 25° C. Winter: About 15 to 30 days at 18 to 20° C.

*Time to produce a rooted young plant.*—Summer: About 28 to 42 days at 20 to 35° C. Winter: About 35 to 56 days at 10 to 20° C.

*Root description.*—Fine to somewhat fibrous; freely branching.

Plant description:

*General appearance.*—Erect and rounded plant growth habit with inflorescences held above the foliage on erect peduncles. Appropriate for 10 and 15-cm containers. Pinching is required to stimulate branching.

*Crop time.*—Moderately fast growth rate; to produce a finished 15-cm containerized plant from rooted cuttings, about 8 to 12 weeks are required.

*Plant height.*—About 25 to 40 cm.

*Plant width.*—About 40 to 70 cm.

*Lateral branch description.*—Length: About 4 to 6.5 cm. Width: About 1.5 mm. Internode length: About 0.6 to 1.6 cm. Texture: Young stems, pubescent; older stems, glabrous. Color: 137A overlain with 82A.

*Foliage description.*—Arrangement: Alternate, single, sessile. Shape: Obovate to elliptical. Apex: Acute to somewhat obtuse. Base: Tapering. Margin: Five to seven lobed with minute teeth. Length: About 1.2 to 5.2 cm. Width: About 0.9 to 3.5 cm. Texture, both surfaces: Glabrous, smooth. Venation pattern: Pinnate. Color: Young leaves, upper surface: 137A. Young leaves, lower surface: 137C. Fully expanded leaves, upper surface: 137A to 139A. Fully expanded leaves, lower surface: 137D. Venation, upper surface: 144B to 144C. Venation, lower surface: 137C.

Inflorescence description:

*Inflorescence form.*—Daisy-type composite inflorescence form. Ray and disc florets arranged acropetally on a capitulum.

*Inflorescence longevity.*—Inflorescences last on the plant for about two to three weeks and for about four to seven days as a cut flower. Inflorescences persistent.

*Natural flowering season.*—Natural flowering season is spring through fall. Plants flower continuously during this period.

*Quantity of inflorescences.*—About two to three inflorescences per lateral branch.

*Inflorescence aspect.*—Mostly flat.

*Inflorescence diameter.*—About 2.5 to 4 cm.

*Inflorescence depth (height).*—About 0.8 to 1 cm.

*Disc diameter.*—About 5 to 8 mm.

*Fragrance.*—None detected.

*Flower bud.*—Shape: Oblate. Length: About 3 mm. Diameter: About 3 mm. Color: 142C to 142D.

*Ray florets.*—Quantity per inflorescence: About 20 to 28 arranged in one to two rows. Aspect: Flat to slightly reflexed. Shape: Lanceolate. Apex: Bluntly acute. Base: Attenuate. Margin: Entire. Length: About 1.2 to 1.7 cm. Width: About 2 to 3 mm. Texture: Smooth, glabrous. Color: When opening, upper surface: 82C. When opening, lower surface: 82B. Mature, upper surface: 85C; fading with subsequent development to 82C. Mature, lower surface: 84D.

*Disc florets.*—Shape: Tubular with five lobes. Length: About 3 mm or shorter. Width: About 1 mm. Color: Immature: 144A. Mature: 153C.

*Phyllaries.*—Quantity per inflorescence: About 15 to 23. Shape: Oblong. Apex: Bluntly acute; fringed. Base: Fused. Margin: Scarious; fringed. Aspect: Concave. Texture: Smooth, satiny. Color: Upper surface: 139C. Lower surface: 139A.

*Peduncle.*—Length: About 5.7 to 8.5 cm. Aspect: Erect. Strength: Moderately strong; inflorescences held erect above foliage. Texture: Smooth. Color: 137B.

*Androecium.*—Present only on disc florets. Stamen number: Five per disc floret. Anther shape: Linear, oblong. Anther color: 11A. Amount of pollen: Moderate to abundant. Pollen color: 6A to 11A.

*Gynoecium.*—Present on both ray and disc florets. Pistil number: One per floret. Style length: About 3 mm. Style color: 155A to 155C. Stigma shape: Bilobed. Stigma color: 10B.

*Seed/fruit.*—Seed and fruit production has occasionally been observed. Seed and fruit typical of species.

Disease/pest resistance: Plants of the new Brachycome have not been observed to be resistant to pathogens and pests common to Brachycomes.

Weather tolerance: Plant of the new Brachycome have been observed to be tolerant to rain and wind conditions. Plants of the new Brachycome have been observed to tolerate temperatures from −4 to 44° C.

It is claimed:

1. A new and distinct cultivar of Brachycome plant named 'Metallic Blue', as illustrated and described.

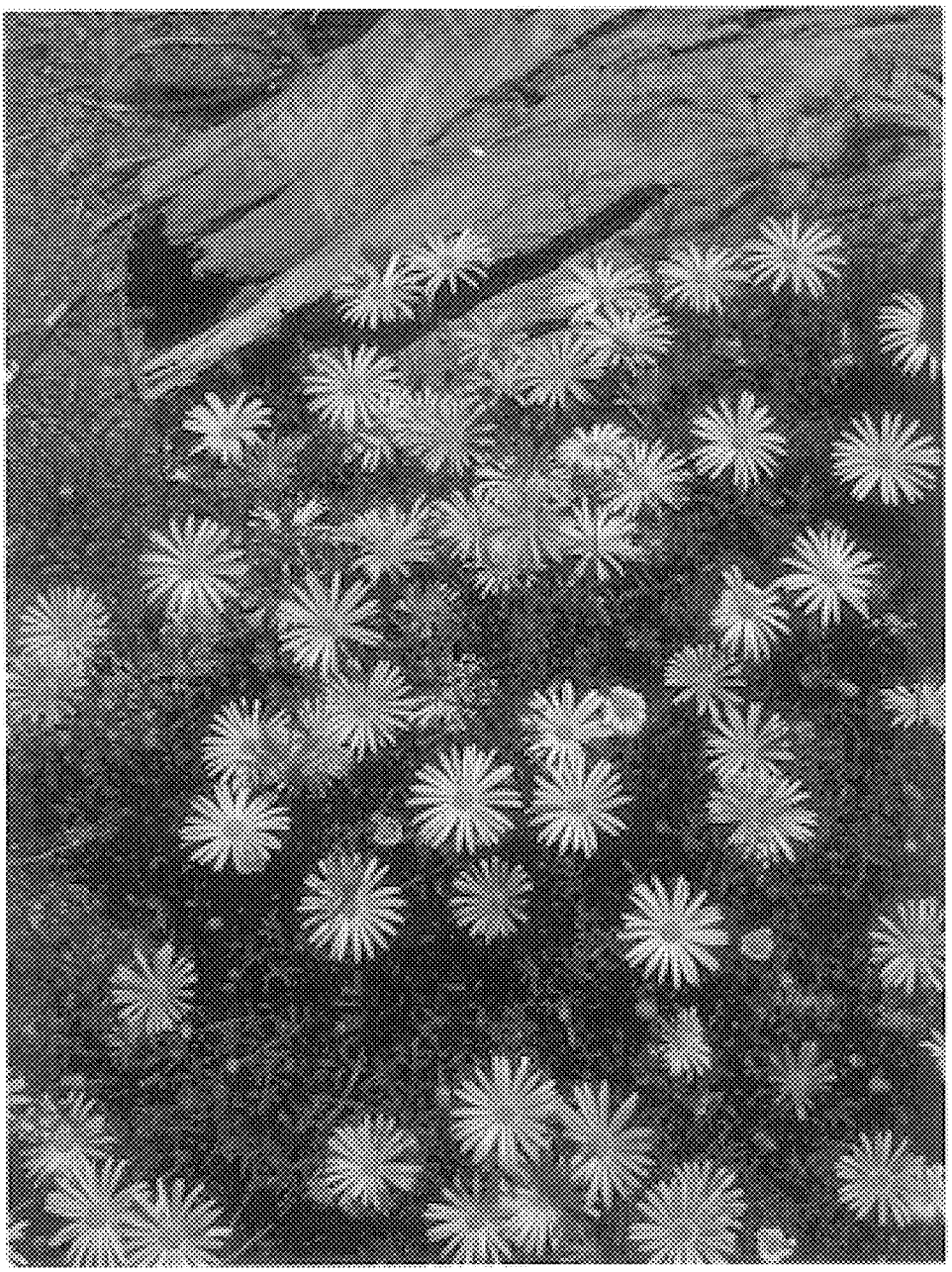

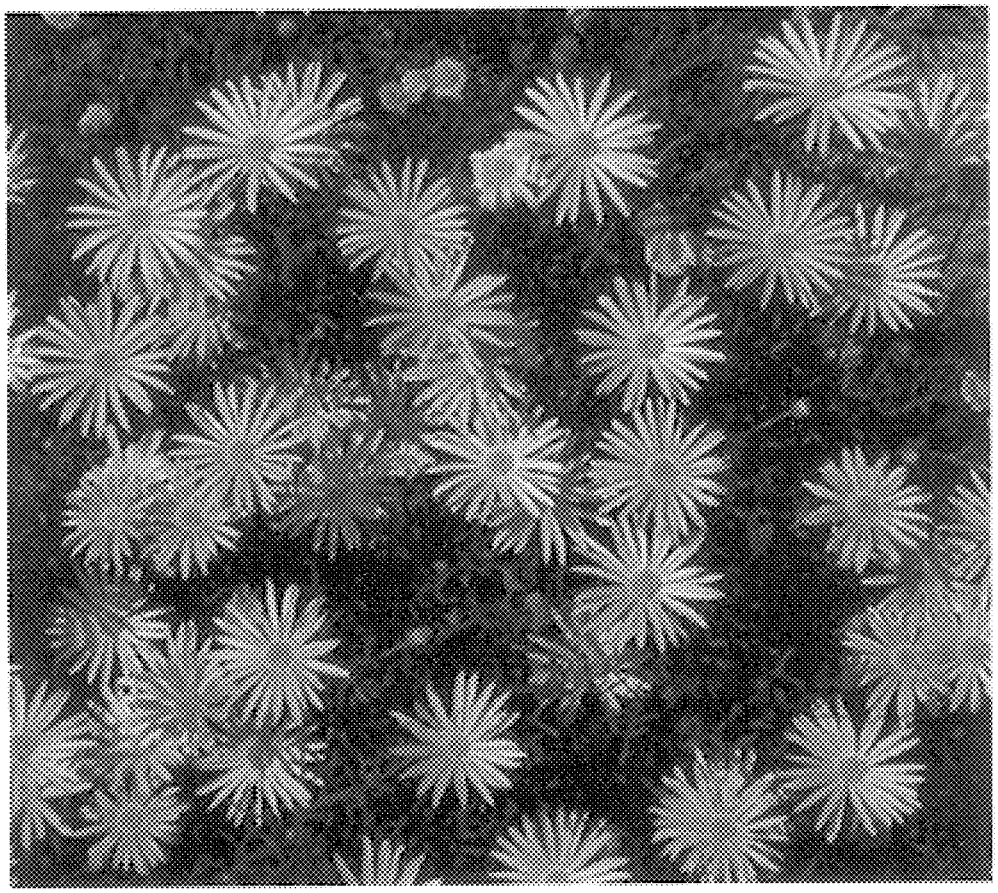

* * * * *